United States Patent
Eom et al.

(10) Patent No.: US 9,616,422 B2
(45) Date of Patent: Apr. 11, 2017

(54) CATALYST COMPOSITION FOR HYDROFORMYLATION REACTION AND METHOD OF HYDROFORMYLATING OLEFIN USING THE SAME

(71) Applicant: LG CHEM, LTD., Seoul (KR)

(72) Inventors: Sung Shik Eom, Daejeon (KR); Dong Hyun Ko, Daejeon (KR); Da Won Jung, Daejeon (KR); Min Soo Kim, Daejeon (KR); Tae Yun Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 108 days.

(21) Appl. No.: 14/426,074

(22) PCT Filed: Sep. 25, 2014

(86) PCT No.: PCT/KR2014/008978
§ 371 (c)(1),
(2) Date: Mar. 4, 2015

(87) PCT Pub. No.: WO2015/046924
PCT Pub. Date: Apr. 2, 2015

(65) Prior Publication Data
US 2016/0256862 A1    Sep. 8, 2016

(30) Foreign Application Priority Data

Sep. 30, 2013 (KR) .................. 10-2013-0115828
Sep. 22, 2014 (KR) .................. 10-2014-0125425

(51) Int. Cl.
| | |
|---|---|
| *C07C 45/54* | (2006.01) |
| *B01J 31/00* | (2006.01) |
| *B01J 31/24* | (2006.01) |
| *C07C 45/50* | (2006.01) |

(52) U.S. Cl.
CPC ............ *B01J 31/2409* (2013.01); *C07C 45/50* (2013.01); *B01J 2231/321* (2013.01); *B01J 2531/821* (2013.01)

(58) Field of Classification Search
CPC .............................. C07C 45/50; B01J 31/2409
USPC .......................................... 568/454; 502/166
See application file for complete search history.

(56) References Cited

U.S. PATENT DOCUMENTS

| | | | |
|---|---|---|---|
| 4,260,828 | A | 4/1981 | Morrell et al. |
| 5,693,832 | A | 12/1997 | Fujita et al. |
| 2008/0281128 | A1 | 11/2008 | Karvinen et al. |
| 2011/0201844 | A1 | 8/2011 | Choi et al. |
| 2012/0059195 | A1 | 3/2012 | Choi et al. |
| 2013/0331612 | A1 | 12/2013 | Ko et al. |

FOREIGN PATENT DOCUMENTS

| | | |
|---|---|---|
| CN | 101160272 A | 4/2008 |
| CN | 103201036 A | 7/2013 |
| EP | 0073398 A1 | 3/1983 |
| JP | 58-39637 A | 3/1983 |
| JP | 5-331156 A | 12/1993 |
| KR | 1020090028251 | 3/2009 |
| KR | 1020100092169 | 8/2010 |
| KR | 1020100092399 | 8/2010 |
| KR | 101089488 B1 | 12/2011 |
| KR | 101095775 | 12/2011 |
| KR | 10-2013-0131516 A | 12/2013 |

*Primary Examiner* — Sikarl Witherspoon
(74) *Attorney, Agent, or Firm* — Dentons US LLP

(57) ABSTRACT

Disclosed are a catalyst composition and a method of hydroformylating olefin using the same, which may maintain catalyst activity through improvement of catalyst stability and reduce a use amount of a ligand while improving selectivity to iso-aldehyde, by using a specific ligand to a transition metal catalyst and a ligand stabilizer together in hydroformylation of olefin.

12 Claims, No Drawings

CATALYST COMPOSITION FOR HYDROFORMYLATION REACTION AND METHOD OF HYDROFORMYLATING OLEFIN USING THE SAME

This application is a National Stage Entry of International Application No. PCT/KR2014/008978, filed Sep. 25, 2014, and claims the benefit of Korean Application No. 10-2013-0115828 filed Sep. 30, 2013 and Korean Application No. 10-2014-0125425 filed Sep. 22, 2014, all of which are hereby incorporated by reference in their entirety for all purposes as if fully set forth herein.

TECHNICAL FIELD

The present invention relates to a catalyst composition for hydroformylation reaction and a method of hydroformylating an olefin using the same. More particular, the present invention relates to a catalyst composition comprising a specific phosphine ligand, a transition metal catalyst, and further a ligand stabilizer used in hydroformylation reaction of an olefin, and a method of hydroformylating olefin using the same.

BACKGROUND ART

Hydroformylation generating linear (normal) and branched (iso) aldehydes, in which the number of carbons increases by 1, by reacting a variety of olefins with a mixture of carbon monoxide (CO) and hydrogen ($H_2$) generally called synthesis gas and in the presence of a homogeneous organometal catalyst and a ligand was first discovered by Otto Roelen of Germany in 1938.

Hydroformylation also known as oxo synthesis is a very important reaction in connection with a homogeneous catalyst reaction. At present, approximately 12 million tons of a variety of aldehydes comprising alcohol derivatives are produced and consumed through oxo synthesis worldwide (SRI report, November 2012, 7000I page 10).

In oxo synthesis, a variety of aldehydes is oxidized or hydrogenated after condensation such as aldol and the like, thereby being transformed into a variety of acids and alcohols comprising long alkyl groups. In particular, hydrogenated alcohols of aldehydes through oxo synthesis are called oxo alcohols. Oxo alcohols are widely used in industry as solvents, additives, raw materials of a variety of plasticizers, synthetic lubricating oils, and the like.

As a catalyst of the hydroformylation reaction, activity of a metal carbonyl compound catalyst was known. Cobalt (Co) and rhodium (Rh) based catalysts are mainly used in industry. An N/I selectivity (ratio of linear (normal) to branched (iso) isomers), activity, and stability of the aldehydes depend on ligand types applied to these catalysts and driving conditions.

At present globally, 70% or more of oxo process-related plants use a low pressure oxo process, in which a large amount of a phosphine ligand is applied to a rhodium based catalyst, due to advantages such as high catalyst activity, a high N/I selectivity, and a relatively easy reaction conditions, in spite of drawbacks such as high catalyst costs, catalyst activity reduction due to poisoning, and the like.

As a central metal of an oxo catalyst, in addition to cobalt (Co) and rhodium (Rh), transition metals such as iridium (Ir), ruthenium (Ru), osmium (Os), platinum (Pt), palladium (Pd), iron (Fe), nickel (Ni), and the like may be used. However, each of the metals is known to have the following catalyst activity relationship: Rh>>Co>Ir, Ru>Os>Pt>Pd>Fe>Ni. CO, Rh, Pt, and Ru, which are Group VIII transition metals, exhibit high catalyst activity in an oxo reaction. Pt and Ru are only used in academic research. At present, rhodium and cobalt are mainly used in most industrial oxo processes. As representative examples, there are $HCo(CO)_4$, $HCo(CO)_3PBu_3$ and $HRh(CO)(PR_3)_3$.

As ligand types used in an oxo process, there are phosphine ($PR_3$, where R is $C_6H_5$, or n-$C_4H_9$), phosphine oxide ($O=P(C_6H_5)_3$), and phosphite. When rhodium is used as a central metal, triphenylphosphine (TPP) as a ligand in connection with catalyst activity and stability is considered to be the best option. Therefore, in most oxo processes, rhodium (Rh) as a catalyst is used and TPP as a ligand is applied. In addition, it is known that TPP as a ligand is applied in an amount of 100 equivalents or more of a catalyst to improve catalyst stability.

Generally, linear aldehyde derivatives of aldehydes, products of an oxo reaction are valuable and, as such, most research on catalysts has focused on increasing a ratio of linear aldehydes.

However, there is an urgent need for technology to improve catalyst stability and reduce a use amount of ligands while improving selectivity for iso-aldehydes.

DISCLOSURE

Technical Problem

Accordingly, inventors of the present invention confirmed that, when a specific phosphine ligand and a specific stabilizer are applied to hydroformylation of olefin, stability of catalyst is improved and a use amount of a ligand is reduced while improving selectivity for iso-aldehyde, during watchful research to overcome the above problems, thus, completing the present invention.

That is, the present invention has been made in view of the above problems, and it is one object of the present invention to provide a catalyst composition comprising a specific phosphine ligand, a transition metal catalyst, and a ligand stabilizer to exhibit superior catalyst activity and improve selectivity of iso-type aldehyde while improving stability of a catalyst and reducing a use amount of a ligand, and a method of hydroformylating olefin using the same.

Technical Solution

In accordance with one aspect of the present invention, provided is a catalyst composition for hydroformylation, comprising a triphenyl phosphine-based compound having a substituent group at a para position, a diphenyl phosphine-based compound, and a transition metal catalyst.

In accordance with another aspect of the present invention, provided is a method of hydroformylating an olefin comprising reacting an olefin and synthesis gas ($CO/H_2$) in the presence of the catalyst composition described above to obtain aldehyde having a normal/iso (N/I) selectivity of 6 or less.

Advantageous Effects

As apparent from the fore-going, the present invention advantageously provides a catalyst composition and a hydroformylation method using the same, which may maintain catalyst activity through improvement of catalyst stability and reduce a use amount of a ligand while improving selectivity for iso-aldehyde, by using a specific ligand to a transition metal catalyst and a ligand stabilizer together in hydroformylation of olefins.

Furthermore, the ligand and the stabilizer may be directly applied to a continuous hydroformylation process to recover aldehyde and oxo synthesis industry.

BEST MODE

Hereinafter, the present invention will be described in more detail.

Since a catalyst composition for hydroformylation of the present invention comprises a specific one-coordinated phosphine compound as a ligand, stability of a catalyst is improved and a use amount of a ligand is reduced in hydroformylation of olefin. As a result, selectivity for iso-aldehydes is improved.

In particular, the catalyst composition for hydroformylation according to the present invention comprises a triphenyl phosphine-based compound having a substituent group at a para position, a diphenyl phosphine-based compound, and a transition metal catalyst.

In one embodiment, the triphenyl phosphine-based compound having the substituent group at the para position may be a compound having a substituent group independently selected from a C1 to C3 alkyl group and a C1 to C5 alkoxy group at the para position.

As a specific embodiment, the triphenyl phosphine-based compound having the substituent group at the para position may be a compound having, at the same time, a substituent group type selected from a C1 to C3 alkyl group and a C1 to C5 alkoxy group at the para position.

As another embodiment, the triphenyl phosphine-based compound having the substituent group at the para position may be one or more selected from tri-p-tolylphosphine (TPTP), tri-p-ethylphenylphosphine (TPEtPP), tris-p-methoxyphenyl phosphine, and tri-p-isopropoxyphenyl phosphine (TIPPP).

In particular, the triphenyl phosphine-based compound having the substituent group at the para position may function as a ligand to the transition metal catalyst in the present invention. In particular, since continuous consumption occurs in an aldehyde recovery process of a hydroformylation continuous process, a selected proper ligand may be added to a reactor. Accordingly, it is easy to apply the triphenyl phosphine-based compound to an actual process. In addition, stability of catalyst may be improved and a use amount of the ligand may be reduced while improving selectivity for iso-aldehyde through combination with a diphenyl-cycloalkyl phosphine-based compound.

The amount of the triphenyl phosphine-based compound having the substituent group at the para position is preferably 0.5 to 200 mole fraction, and may be 1 to 100 mole fraction or 5 to 50 mole fraction, with respect to 1 mol of a central metal of the transition metal catalyst. When the amount of the triphenyl phosphine-based compound is smaller than the lowest amount, reactivity of the catalyst may not be exhibited due to lack of the ligand. On the other hand, when the amount of the triphenyl phosphine-based compound is larger than the largest amount, a reaction rate may not be improved due to a large amount of the compound.

In one embodiment, the amount of the triphenyl phosphine-based compound having the substituent group at the para position may be 0.5 to 6.0 wt %, or 1.0 to 5.0 wt % with respect to a total weight of the catalyst composition. When the amount of the triphenyl phosphine-based compound is smaller than the lowest amount, catalyst stability may be affected. On the other hand, when the amount of the triphenyl phosphine-based compound is larger than the largest amount, costs increase due to overuse of the expensive compound.

The triphenyl phosphine-based compound having the substituent group at the para position may comprise tri-p-tolylphosphine (TPTP) in an amount of 1.0 to 5.0 wt %, or 1.0 to 4.0 wt %, with respect to a total weight of the catalyst composition.

Meanwhile, when a triphenyl phosphine-based compound (TPP), that is not substituted at the para position, is used, improved selectivity for iso-aldehyde may not be accomplished whenever the triphenyl phosphine-based compound (TPP) is used alone or with the diphenyl phosphine-based compound as a stabilizer.

In one embodiment, the diphenyl phosphine-based compound may comprise a C1 to C6 n-alkyl group, a C2 to C6 branched alkyl group, a C3 to C6 tert-alkyl group, or a C5 to C6 cycloalkyl group.

As a specific embodiment, the diphenyl phosphine-based compound comprises a C1 to C6 n-alkyl group, a C2 to C6 branched alkyl group, a C3 to C6 tert-alkyl group, or a C5 to C6 cycloalkyl group, and may have a substituent group independently selected from a C1 to C3 alkyl group and a C1 to C5 alkoxy group at the para position of diphenyl.

As another embodiment, the diphenyl phosphine-based compound may be 1 or more selected from n-alkyl diphenylphosphine, branched alkyl diphenylphosphine, tert-butyl diphenylphosphine, cyclohexyldiphenylphosphine, cyclohexylditolyl phosphine, and cycloheptyldiphenylphosphine.

As yet another embodiment, the diphenyl phosphine-based compound may be 1 or more selected from cyclohexyldiphenylphosphine, cyclohexylditolyl phosphine, and cycloheptyldiphenylphosphine.

In particular, the diphenyl phosphine-based compound of the present invention may function as a ligand stabilizer.

The amount of the diphenyl phosphine-based compound is preferably 1 to 250 mole fraction, and may be 10 to 100 mole fraction or 10 to 60 mole fraction, with respect to 1 mol of a central metal of the transition metal catalyst. When the amount of the diphenyl phosphine-based compound is smaller than the lowest amount, effects of stabilizing the ligand may be insignificant. On the other hand, when the amount of the diphenyl phosphine-based compound is larger than the largest amount, a reaction rate may not be improved due to a large amount of the compound.

In one embodiment, the amount of the diphenyl phosphine-based compound may be 0.5 to 6.0 wt % or 1.0 to 5.5 wt %, with respect to a total weight of the catalyst composition. When the amount of the diphenyl phosphine-based compound is smaller than the lowest amount, catalyst stability may be deteriorated. On the other hand, when the amount of the diphenyl phosphine-based compound is larger than the largest amount, costs increase due to overuse of the expensive compound.

The diphenyl phosphine-based compound may comprise cyclohexyldiphenylphosphine (CDHP) in an amount of 1.0 to 5.5 wt % or 1.0 to 5.0 wt %, with respect to a total weight of the catalyst composition.

In one embodiment, the transition metal catalyst may be represented by Formula 1 below:

$$M(L1)_x(L2)_y(L3)_z \qquad \text{[Formula 1]}$$

wherein M is rhodium (Rh), iridium (Ir) or cobalt (Co), and $L^1$, $L^2$ and $L^3$ are each independently hydrogen, CO, cyclooctadiene, norbornene, chlorine, triphenylphosphine, or acetylacetonate, x, y and z are each independently integer of 0 to 5, and at least one of x, y and z is not 0.

As a specific embodiment, the transition metal catalyst may be one or more selected from cobalt carbonyl [$Co_2(CO)_8$], acetylacetonate dicarbonyl rhodium [$Rh(AcAc)(CO)_2$], acetylacetonate carbonyl triphenylphosphine rhodium [$Rh(AcAc)(CO)(TPP)$], hydrido carbonyl tri(triphenylphosphine)rhodium [$HRh(CO)(TPP)_3$], acetylacetonate dicarbonyl iridium [$Ir(AcAc)(CO)_2$], and hydrido carbonyl tri(triphenylphosphine)iridium [$HIr(CO)(TPP)_3$].

The amount of a central metal of the transition metal catalyst may be 10 to 1000 ppm, or 50 to 500 ppm based on a weight or volume of the central metal of the catalyst composition. The amount of the central metal of less than 10 ppm is industrially undesirable since hydroformylation rate reduces. On the other hand, when the amount of the central metal is larger than 1000 ppm, costs increase due to expressive central metal and a reaction rate may not be proper.

In one embodiment, a method of hydroformylating the olefin using the catalyst composition may comprise obtaining aldehyde having a normal/iso (N/I) selectivity of 6 or less by reacting an olefin and synthesis gas ($CO/H_2$) in the presence of the catalyst composition.

In one embodiment, the olefin may comprise a compound represented by Formula 2 below:

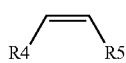

[Formula 2]

wherein $R_4$ and $R_5$ are each independently hydrogen, a C1 to C20 alkyl group, fluorine (F), chlorine (Cl), a bromo (Br) group, trifluoromethyl group (~$CF_3$) or a C6 to C20 aryl group having 0 to 5 substituent groups, and a substituent group of the aryl group is a nitro $NO_2$) group, fluorine (F), chlorine (Cl), bromine (Br), a methyl group, an ethyl group, a propyl group, or a butyl group.

As a specific embodiment, the olefin may be one or more selected from ethene, propene, 1-butene, 1-pentene, 1-hexene, 1-octene, and styrene.

The synthesis gas used in the method of preparing aldehyde of the present invention is mixed gas of carbon monoxide and hydrogen. A mixing ratio of $CO:H_2$ may be 5:95 to 70:30, 40:60 to 60:40, or 50:50 to 40:60, but the mixing ratio is not limited thereto. When the mixing ratio is outside these ranges, unused gas is accumulated in a reactor and, as such, reactivity of the catalyst may be deteriorated.

In addition to the method of hydroformylating the olefin according to the present invention, other reaction conditions may be carried out through generally known methods.

In the method of preparing aldehyde of the present invention, a reaction temperature of the olefin and the synthesis gas ($CO/H_2$) in the presence of the catalyst composition may, for example, be 20 to 180° C., 50 to 150° C., or 75 to 125° C., but the present invention is not limited thereto. When the reaction temperature is less than 20° C., hydroformylation does not proceed. On the other hand, when the reaction temperature is larger than 180° C., stability of the catalyst is seriously damaged and, as such, activity of the catalyst is deteriorated.

In addition, pressure of the reaction may, for example, be 1 to 700 bar, 1 to 300 bar, or 5 to 30 bar. When the reaction pressure is less than 1 bar, the hydroformylation reaction proceeds too slowly. On the other hand, when the reaction pressure is larger than 700 bar, an expensive reactor must be used to prevent explosion, without improvement of activity, and, thus, industrialization may be difficult.

When the process of hydroformylating the olefin according to the present invention is schematically described, the triphenyl phosphine-based compound having the substituent group at the para position, a transition metal catalyst (b), and a diphenyl-cycloalkyl phosphine-based compound are dissolved in a solvent such as benzene, toluene, ethanol, pentanol, octanol, texanol, butyraldehyde, pentyl aldehyde, or the like, to prepare a mixed solution. Subsequently, the olefin, and the synthesis gas of carbon monoxide and hydrogen with the mixed solution are added to the reactor and then hydroformylation is proceeded by elevating temperature and applying pressure, while stirring. As a result, iso-aldehyde having improved selectivity, particularly having a normal/iso (N/I) selectivity of 6 or less may be obtained.

Concrete ingredients and contents of the catalyst composition according to the present invention are the same as described above. The catalyst composition of the present invention may be prepared by dissolving in the solvent described above. A solvent used in the present invention is preferably one or more selected from aldehydes comprising propane aldehyde, butyraldehyde, pentyl aldehyde, valer aldehyde, and the like; ketones comprising acetone, methyl ethyl ketone, methyl isobutyl ketone, acetophenone, cyclohexanone, and the like; alcohols comprising ethanol, pentanol, octanol, texanol, and the like; aromatic compounds comprising benzene, toluene, xylene, and the like; halogenated aromatic compounds comprising ortho-dichlorobenzene, and the like; ethers comprising tetrahydrofuran, dimethoxyethane, dioxane, and the like; halogenated paraffins comprising methylene chloride and the like; and paraffin hydrocarbons comprising heptane and the like, but the present invention is not limited thereto. In particular, the solvent may be an aldehyde generated through hydroformylation.

In accordance with the catalyst composition and the method of hydroformylating olefin using the same of the present invention, although the ligand is used in a smaller amount than a conventionally used amount, an N/I selectivity of aldehyde is 3.1 to 3.7 and, thus, selectivity for iso-aldehyde is improved. In addition, a stabilization value of the catalyst is 60 to 61% after 15 hr, 72 to 80% after 5 hr, and 78 to 92% after 2.5 hr, based on a catalyst activity value of 116 to 138% during supply of fresh.

Hereinafter, preferred examples will be provided for better understanding of the present invention. It will be apparent to those skilled in the art that these examples are only provided to illustrate the present invention and various modifications and alterations are possible within the scope and technical range of the present invention. Such modifications and alterations fall within the scope of claims included herein.

EXAMPLE 1

250 ppm of rhodium (Rh) as a transition metal catalyst, 2.0 wt % of a triphenyl phosphine-based compound (tri-p-tolylphosphine), a substituent group at a para position of which is methyl, as a ligand to the catalyst, and 2.0 wt % of a diphenyl phosphine-based compound (cyclohexyl diphenyl phosphine) having a C6 cycloalkyl group, as a ligand stabilizer were dissolved in butylaldehyde to prepare 100 g of a total solvent.

Mixed gas of propene:CO:H$_2$ mixed in a molar ratio of 1:1:1 was added to the catalyst solution, and stirred for 1 hour at 90° C. while maintaining pressure of the reactor at 8 bar such that a reaction was carried out.

Activity (%) of the fresh catalyst used in the reaction and a normal/iso selectivity of aldehyde prepared were measured according to methods described below. In addition, a degree of stability of the catalyst was measured maximally up to 15 hr through a stability test. Results are summarized in Tables 1 and 2.

<Measurement of Properties>

Catalyst activity (%): a total amount of aldehyde generated in the reaction was measured by dividing into a molecular weight of butyraldehyde, a concentration of the used catalyst, and reaction time. A unit was mol (BAL)/mol(Rh)/h.

Normal/iso selectivity of aldehyde: resultant values are values obtained by dividing the amount of normal-butyraldehyde generated from the reaction into the amount of iso-butyraldehyde. A generation amount of each aldehyde was measured through gas chromatography (GC).

Stability test (againg test): mixed gas of CO and H$_2$ mixed in a molar ratio of 1:1 was added to the solution to maintain pressure of the reactor pressure at 10 bar and an aging test was carried out while stirring at 120° C. Aging activity change of the catalyst was recorded in %.

EXAMPLE 2

An experiment was carried out in the same manner as in Example 1, except that 1.0 wt % of the triphenyl phosphine-based compound (tri-p-tolylphosphine), in which a substituent group at a para position is methyl, and 2.5 wt % of the diphenyl phosphine-based compound (cyclohexyl diphenyl phosphine) having a C6 cycloalkyl group, as a ligand stabilizer were used. Measured results are summarized in Tables 1 and 2.

COMPARATIVE EXAMPLE 1

An experiment was carried out in the same manner as in Example 1, except that 4.0 wt % of the triphenyl phosphine-based compound (tri-p-tolylphosphine), in which a substituent group at a para position is methyl, was used and the diphenyl phosphine-based compound (cyclohexyl diphenyl phosphine) having a C6 cycloalkyl group, as a ligand stabilizer was not added. Measured results are summarized in Tables 1 and 2.

COMPARATIVE EXAMPLE 2

An experiment was carried out in the same manner as in Example 1, except that 6.0 wt % of triphenyl phosphine, in which a substituent group does not exist at a para position, was used instead of the triphenyl phosphine-based compound (tri-p-tolylphosphine), in which a substituent group at a para position is methyl, and the diphenyl phosphine-based compound (cyclohexyl diphenyl phosphine) having a C6 cycloalkyl group, as a ligand stabilizer was not added. Measured results are summarized in Tables 1 and 2.

TABLE 1

| Classification | Ligand | Stabilizer of ligand | Fresh catalyst activity (%) | Normal/iso selectivity |
|---|---|---|---|---|
| Example 1 | Triphenyl phosphine-based compound, in which substituent group at para position is methyl | Diphenyl-cycloalkylphosphine, which comprises C6 cycloalkyl and in which substituent group does not exist at para position | 116 | 3.7 |
| Example 2 | | | 138 | 3.1 |
| Comparative Example 1 | — | | 98 | 6.4 |
| Comparative Example 2 | Triphenyl phosphine, in which substituent group does not exist at para position | | 100 | 9.1 |

TABLE 2

| Classification | Ligand | Stabilizer of ligand | Fresh | Catalyst stability test (aging time) 2.5 hr | 5.0 hr | 15.0 hr |
|---|---|---|---|---|---|---|
| Example 1 | Triphenyl-phosphine, based compound, in which substituent group at para position is methyl | Diphenyl-cycloalkyl-phosphine-which comprises C6 cycloalkyl and in which substituent group does not exist at para position | 116 | 78 | 72 | 60 |
| Example 2 | | | 138 | 92 | 80 | 61 |
| Comparative Example 1 | — | | 98 | 63 | 59 | 54 |
| Comparative Example 2 | Triphenyl-phosphine, in which substituent group does not exist at para position | | 100 | 56 | 48 | 28 |

As shown in Tables 1 and 2, it can be confirmed that, in Example 1 to 2 using the specific ligand and the stabilizer to the ligand together of the present invention, iso-aldehyde selectivity of aldehyde, an N/I selectivity of which is 3.1 to 3.7, is improved, and catalyst stability is dramatically improved showing 60 to 61% after 15 hr, 72 to 80% after 5 hr, and 78 to 92% after 2.5 hr, based on a catalyst activity value of 116 to 138% during supply of fresh.

On the other hand, it can be confirmed that, in Comparative Example 1 using only the ligand, without the stabilizer, in a total amount of the ligand and the stabilizer used in Examples 1 to 2, an N/I selectivity of aldehyde is 6.4 (an N/I selectivity of less than 6 is impossible) due to relative reduction of iso-aldehyde selectivity, and a stability value of the catalyst is reduced indicating 54% after 15 hr, 59% after 5 hr, and 63% after 2.5 hr, based on a catalyst activity value of 98% during supply of fresh.

Furthermore, it can be confirmed that, in Comparative Example 2 using only triphenylphosphine in which a substituent group does not exist at a para position, conventionally used instead of the ligand used in Examples 1 to 2, normal aldehyde selectivity is improved indicating an aldehyde N/I selectivity of 9.1, and a stability value of the catalyst poorly is 28% after 15 hr, 48% after 5 hr, and 56% after 2.5 hr, based on a catalyst activity value of 100% during fresh supply.

What is claimed is:

1. A catalyst composition for hydroformylation reaction, comprising a triphenyl phosphine-based compound having a substituent group at a para position, a diphenyl phosphine-based compound, and a transition metal catalyst,
    wherein the triphenyl phosphine-based compound having the substituent group at the para position comprises tri-p-tolylphosphine (TPTP) in an amount of 1.0 to 5.0 wt % with respect to a total weight of the catalyst composition, and
    wherein the diphenyl phosphine-based compound comprises cyclohexyldiphenylphosphine in an amount of 1.0 to 5.0 wt % with respect to a total weight of the catalyst composition.

2. The catalyst composition according to claim 1, wherein the transition metal catalyst is represented by Formula 1 below:

M(L1)x(L2)y(L3)z    [Formula 1]

wherein M is rhodium (Rh), iridium (Ir) or cobalt (Co), and
    $L^1$, $L^2$ and $L^3$ are each independently hydrogen, CO, cyclooctadiene, norbornene, chlorine, triphenylphosphine, or acetylacetonate, x, y and z are each independently integer of 0 to 5, and at least one of x, y and z is not 0.

3. The catalyst composition according to claim 1, wherein the transition metal catalyst is one or more selected from cobalt carbonyl [$Co_2(CO)_8$], acetylacetonate dicarbonyl rhodium [Rh(AcAc)(CO)$_2$], acetylacetonate carbonyl triphenylphosphine rhodium [Rh(AcAc)(CO)(TPP)], hydrido carbonyl tri(triphenylphosphine)rhodium [HRh(CO)(TPP)$_3$], acetylacetonate dicarbonyl iridium [Ir(AcAc)(CO)$_2$], and hydrido carbonyl tri(triphenylphosphine)iridium [HIr(CO)(TPP)$_3$].

4. The catalyst composition according to claim 1, wherein an amount of a central metal of the transition metal catalyst is 10 to 1000 ppm based on a weight or volume of the catalyst composition.

5. The catalyst composition according to claim 1, wherein an amount of the triphenyl phosphine-based compound having the substituent group at the para position is 0.5 to 200 mole fraction with respect to 1 mol of a central metal of the transition metal catalyst.

6. The catalyst composition according to claim 1, wherein an amount of the diphenyl phosphine-based compound is 1 to 250 mole fraction with respect to 1 mol of a central metal of the transition metal catalyst.

7. A method of hydroformylating an olefin, the method comprising obtaining an aldehyde having a normal/iso (N/I) selectivity of 6 or less by reacting an olefin and synthesis gas (CO/H$_2$) in the presence of the catalyst composition according to claim 1.

8. The method according to claim 7, wherein the olefin comprises a compound represented by Formula 2 below:

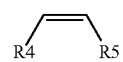

[Formula 2]

wherein $R_4$ and $R_5$ are each independently hydrogen, a C1 to C20 alkyl group, fluorine (F), chlorine (Cl), bromine (Br), trifluoromethyl (—CF$_3$) or a C6 to C20 aryl group having 0 to 5 substituent groups, and
    a substituent group of the aryl group is a nitro (—NO$_2$) group, fluorine (F), chlorine (Cl), bromine (Br), a methyl group, an ethyl group, a propyl group, or a butyl group.

9. The method according to claim 7, wherein the olefin is one or more selected from ethene, propene, 1-butene, 1-pentene, 1-hexene, 1-octene, and styrene.

10. The method according to claim 7, wherein a molar ratio of the synthesis gas (Co:H$_2$) is 5:95 to 70:30.

11. The method according to claim 7, wherein the catalyst composition is added to a next reaction after dissolving the catalyst composition in one or more or more selected from propane aldehyde, butyraldehyde, pentyl aldehyde, valer aldehyde, acetone, methyl ethyl ketone, methyl isobutyl ketone, acetophenone, cyclohexanone, ethanol, pentanol, octanol, texanol, benzene, toluene, xylene, ortho dichlorobenzene, tetrahydrofuran, dimethoxyethane, dioxane, methylene chloride, and heptane.

12. The method according to claim 7, wherein the reaction is carried out at 20 to 180° C. at a pressure of 1 to 700 bar.

* * * * *